United States Patent
Lin et al.

(10) Patent No.: US 8,466,301 B2
(45) Date of Patent: Jun. 18, 2013

(54) ORGANIC DYE AND DYE-SENSITIZED SOLAR CELL USING THE SAME

(75) Inventors: Jiann Tsuen Lin, Taipei (TW); Yung-Sheng Yen, Taoyuan County (TW); Ying-Chan Hsu, Tainan County (TW); Ming-Chang Yeh, Taipei (TW); Pin-Cheng Chen, Taipei County (TW)

(73) Assignees: Academia Sinica, Taipei (TW); Plasmag Technology Inc., Shing-Chu (TW)

( * ) Notice: Subject to any disclaimer, the term of this patent is extended or adjusted under 35 U.S.C. 154(b) by 698 days.

(21) Appl. No.: 12/508,574

(22) Filed: Jul. 24, 2009

(65) Prior Publication Data
US 2010/0275986 A1   Nov. 4, 2010

(30) Foreign Application Priority Data
Apr. 29, 2009   (TW) ................ 98114228 A

(51) Int. Cl.
*C07D 307/54*   (2006.01)
*C07D 409/04*   (2006.01)

(52) U.S. Cl.
USPC .................. 549/496; 549/59; 323/906

(58) Field of Classification Search
USPC ...................... 549/59, 496; 323/906
See application file for complete search history.

(56) References Cited

FOREIGN PATENT DOCUMENTS
TW   200712136   4/2007

OTHER PUBLICATIONS

Lin et al. "Organic Dyes Containing Furan Moiety for High-Performance Dye-Sensitized Solar Cells", Organic Letters, 2009, vol. 11, No. 1, pp. 97-100.*

D. Bogdal, "Synthesis of Polymethacrylates with Carbazole and Benzofuran Pendant Groups for Photovoltaic Applications," Wiley-VCH Verlag GmbH & Co. KGaA, Weinheim, Macromol. Symp. 2008, 268, pp. 48-52.

Il Jung et al., "Synthesis and Photovoltaic Properties of Efficient Organic Dyes Containing the Benzo[b]furan Moiety for Solar Cells," American Chemical Society, Mar. 30, 2007, J. Org. Chem. 2007, 72, pp. 3652-3658.

Daniel P. Hagberg, et al., "A novel organic chromophore for dye-sensitized nanostructured solar cells", Chem. Commun., Apr. 13, 2006, pp. 2245-2247.

Sanghoon Kim, et al., "Molecular engineering of organic sensitizers for solar cell applications", J. Am. Chem. Soc. (JACS), vol. 128, Dec. 5, 2006, pp. 16701-16707.

"Office Action of Taiwan Counterpart Application", issued on Aug. 16, 2012, p. 1-p. 7.

* cited by examiner

*Primary Examiner* — Joseph Kosack
(74) *Attorney, Agent, or Firm* — Jianq Chyun IP Office

(57) ABSTRACT

An organic dye used in a dye-sensitized solar cell is described, having general formula (1):

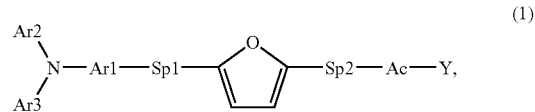

wherein Ar1 represents a substituted or unsubstituted arylene group, Ar2 and Ar3 each independently represent a substituted or unsubstituted aryl group, Sp1 represent a single bond or a spacer group allowing conjugation between Ar1 and the furan moiety, Sp2 represent a single bond or a spacer group allowing conjugation between the furan moiety and Ac, Ac represents an acceptor group, and Y represents an anchoring group.

12 Claims, 1 Drawing Sheet

ORGANIC DYE AND DYE-SENSITIZED SOLAR CELL USING THE SAME

CROSS-REFERENCE TO RELATED APPLICATION

This application claims the priority benefit of Taiwan application serial no. 98114228, filed on Apr. 29, 2009. The entirety of the above-mentioned patent application is hereby incorporated by reference herein and made a part of specification.

BACKGROUND OF THE INVENTION

1. Field of the Invention

The present invention relates to a material of a solar cell. More particularly, the present invention relates to an organic dye of a dye-sensitized solar cell (DSSC) and a DSSC using the same.

2. Description of Related Art

The increasing demand for power supply as well as environmental concern for the consumption of fossil fuel have triggered global research on the development of clean and renewable energy sources. Among possible alternates for fossil fuel energy, solar energy appears to be very attractive: covering 0.16% of the land of the Earth with 10% efficient solar conversion systems would provide power nearly twice the world's consumption rate of fossil energy. Though silicon- and other semiconductor-based solar cells (known as photovoltaic cells) have dominated the solar cell market for decades, DSSCs have also attracted considerable interest ever since the breakthrough made by Grätzel and co-workers (O'Regan, B.; Grätzel, M. Nature 1991, 353, 737). Efficiency record of about 11% has been achieved with ruthenium-based sensitizers developed by Grätzel and other groups. Though being developed later than ruthenium dyes, metal-free sensitizers also attract much attention and a high efficiency of about 9% has also been achieved for DSSCs based on a metal-free sensitizer.

Various metal-free dyes have been used for the construction of DSSCs. The inventors have reported metal-free sensitizers which consisted of an arylamine as the electron donor, a 2-cyanoacrylic acid as the electron acceptor, and a conjugated bridge containing thiophene moieties. Compared with benzenoid moieties, the thiophene can provide more effective conjugation and lower the energy of the charge transfer transition because of its smaller resonance energy (thiophene, 29 kcal mol$^{-1}$; benzene, 36 kcal mol$^{-1}$).

SUMMARY OF THE INVENTION

Accordingly, it is interesting to incorporate a furan moiety with smaller resonance energy (26 kcal mol$^{-1}$) in a bridge of a dye.

The present invention is directed to an organic dye used in a DSSC, wherein the bridge has furan moiety.

The present invention is directed to a DSSC in which the organic dye of the invention is used.

In the present invention, an organic dye used in a DSSC has general formula (1):

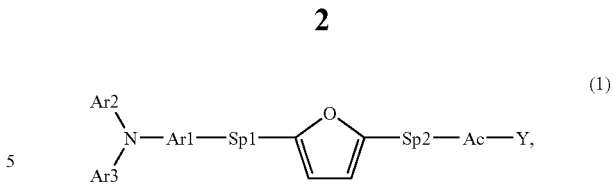

wherein Ar1 represents a substituted or unsubstituted arylene group, Ar2 and Ar3 each independently represent a substituted or unsubstituted aryl group, Sp1 represent a single bond or a spacer group allowing conjugation between Ar1 and the furan moiety, Sp2 represent a single bond or a spacer group allowing conjugation between the furan moiety and Ac, Ac represents an acceptor group, and Y represents an anchoring group, wherein if Ar2 or Ar3 represents a substituted aryl group, a substituted group of said substituted aryl group is selected from the group consisting of alkyl having 1~5 carbon atom(s) and alkoxy having 1~5 carbon atom(s).

According to an embodiment, said Ar1 represents a substituted or unsubstituted 1,4-phenyl, 2,7-fluorene or 2,7-carbazole. A substituted group of said substituted or unsubstituted 1,4-phenyl, 2,7-fluorene or 2,7-carbazole is selected from the group consisting of alkyl having 1~5 carbon atom(s) and alkoxy having 1~5 carbon atom(s). In particular, at least one of 2-position and 5-position of 1,4-phenyl is substituted by alkyl or alkoxy, and 9-position of 2,7-fluorene is substituted by at least one alkyl. For example, 9-position of 2,7-fluorene is substituted by two ethyl.

According to an embodiment, Ar2 and Ar3 each independently represent a substituted or unsubstituted phenyl, 2-fluorenyl, 1-naphthyl, 9-anthracenyl, 1-pyrenyl or 2-carbazolyl. Ar2 and Ar3 can both be phenyl or 2-fluorenyl.

According to an embodiment, the spacer group Sp1 and the spacer group SP2 each independently represent vinylene, cyanovinylene or 2,5-thiophene group.

According to an embodiment, the acceptor group Ac represents 2-cyanoethenyl.

According to an embodiment, the anchoring group Y comprises a carboxylic acid group.

According to an embodiment, the combination of the acceptor group Ac and the anchoring group Y comprises 2-cyanoacrylic acid group.

According to an embodiment, the organic dye used in the DSSC has formula (2), (3), (4) or (5), wherein 4-positions of Ar2 and Ar3 are each independently substituted by alkyl having 1~5 carbon atom(s) or alkoxy having 1~5 carbon atom(s).

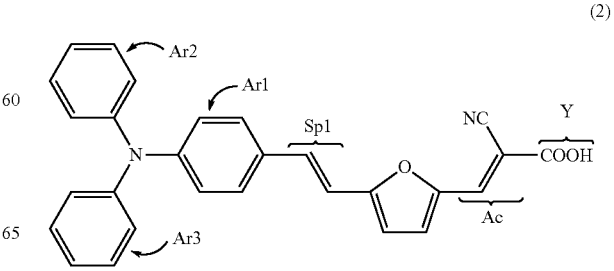

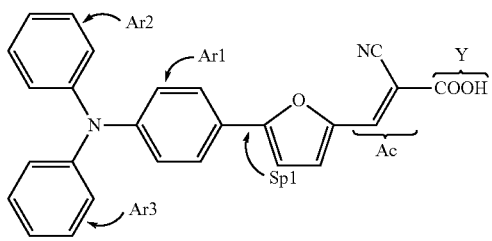

(3)

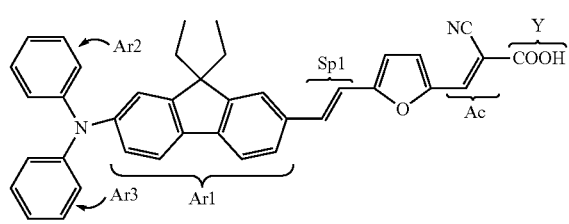

(4)

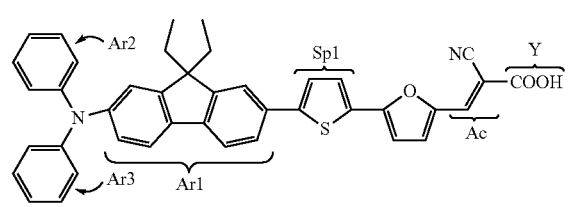

(5)

A DSSC comprising an organic dye as above mentioned, an electrolyte and photo-electrodes is also provided.

The DSSC of the present invention uses the organic dye having furan moiety, and the performance of the organic dye is quite close to that of the ruthenium-based dye. Because ruthenium is not needed in the present invention, the cost of the organic dye and DSSC using the same is greatly lower than that of the ruthenium-based dye and ruthenium-based DSSC.

In order to make the aforementioned and other features and advantages of the present invention more comprehensible, several embodiments accompanied with figures are described in detail below.

BRIEF DESCRIPTION OF THE DRAWINGS

The accompanying drawings constituting a part of this specification are incorporated herein to provide a further understanding of the invention. Here, the drawings illustrate embodiments of the invention and, together with the description, serve to explain the principles of the invention.

DESCRIPTION OF EMBODIMENTS

Figure 1:
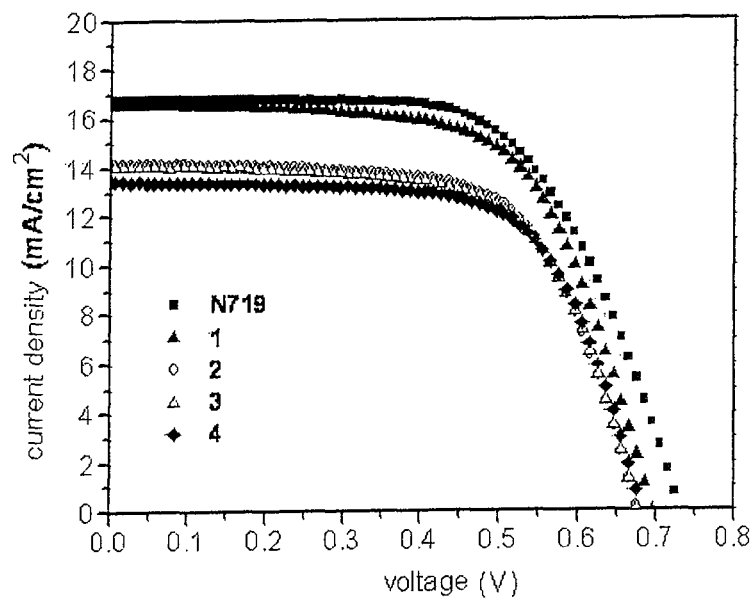
FIG. 1 shows photocurrent-voltage (J-V) curves of the dyes in examples 1-4.

An organic dye used in a dye-sensitized solar cell, having general formula (1):

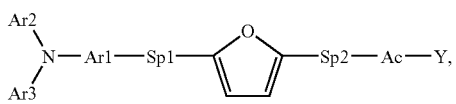

(1)

wherein Ar1 represents a substituted or unsubstituted arylene group, Ar2 and Ar3 each independently represent a substituted or unsubstituted aryl group, Sp1 represent a single bond or a spacer group allowing conjugation between Ar1 and the furan moiety, Sp2 represent a single bond or a spacer group allowing conjugation between the furan moiety and Ac, Ac represents an acceptor group, and Y represents an anchoring group, wherein if Ar2 or Ar3 represents a substituted aryl group, a substituted group of the substituted aryl group is selected from the group consisting of alkyl having 1~5 carbon atom(s) and alkoxy having 1~5 carbon atom(s).

According to an embodiment, said Ar1 represents a substituted or unsubstituted 1,4-phenyl, 2,7-fluorene or 2,7-carbazole. A substituted group of said substituted or unsubstituted 1,4-phenyl, 2,7-fluorene or 2,7-carbazole is selected from the group consisting of alkyl having 1~5 carbon atom(s) and alkoxy having 1~5 carbon atom(s). In particular, at least one of 2-position and 5-position of 1,4-phenyl is substituted by alkyl or alkoxy, and 9-position of 2,7-fluorene is substituted by at least one alkyl. For example, 9-position of 2,7-fluorene is substituted by two ethyl. Ar2 and Ar3 each independently represent a substituted or unsubstituted phenyl, 2-fluorenyl, 1-naphthyl, 9-anthracenyl, 1-pyrenyl or 2-carbazolyl. Ar2 and Ar3 can both be phenyl or 2-fluorenyl. If Ar2 and Ar3 both represent phenyl, 4-positions of Ar2 and Ar3 are each independently substituted by alkyl having 1~5 carbon atom(s) or alkoxy having 1~5 carbon atom(s). The spacer group Sp1 and the spacer group SP2 each independently represent vinylene, cyanovinylene or 2,5-thiophene group. Moreover, the combination of the acceptor group Ac and the anchoring group Y comprises 2-cyanoacrylic acid group.

EXAMPLES

Four organic dyes of four examples of the present invention are as following compounds:

1

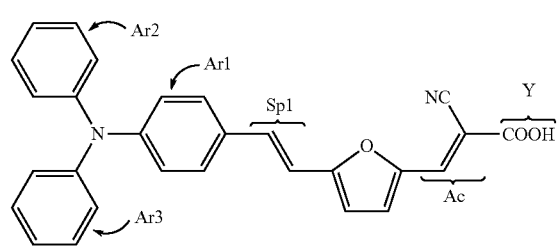

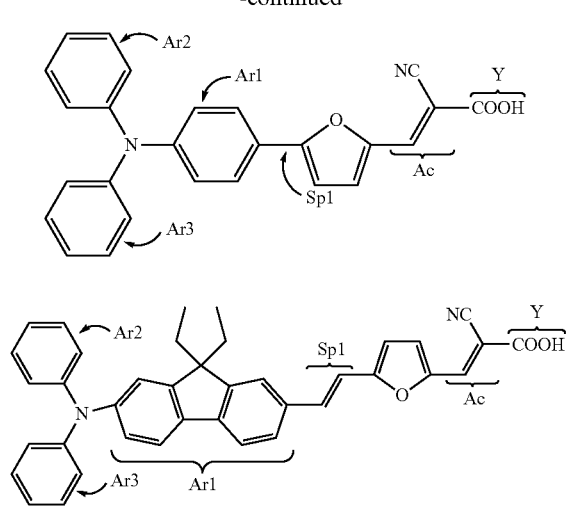
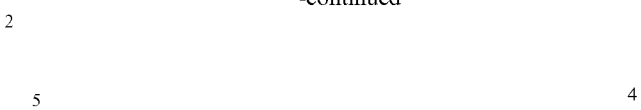
Compounds 1-4 can be synthesized by synthesis scheme 1.
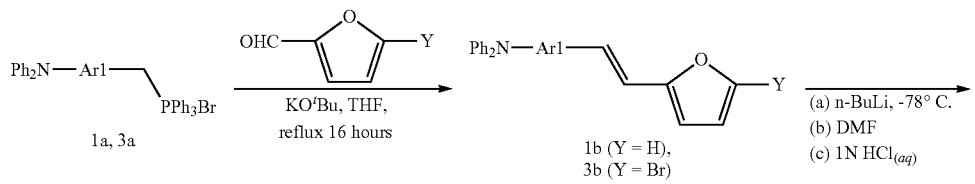
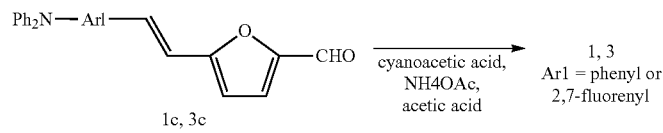
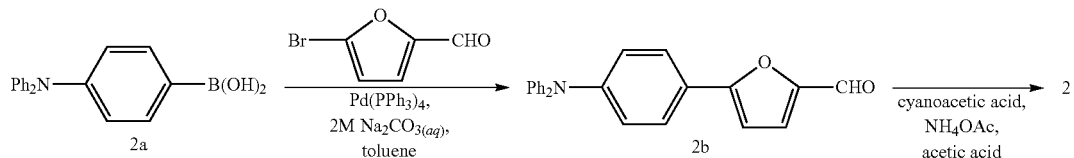
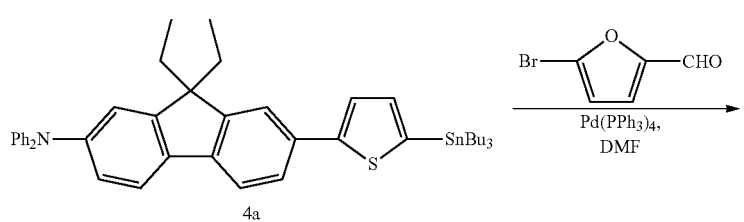
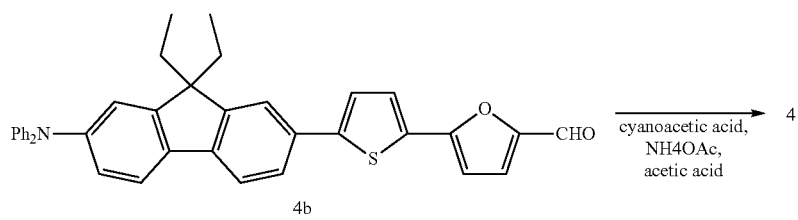

Compounds 1, 3 are synthesized from Wittig reagents containing a triphenylamine or a diphenylamino-2-fluorene moiety. Reactions of these Wittig reagents with 2-furaldehyde provided intermediates 1b and 3b, which underwent formylation to form 1c and 3c. The desired products were obtained from the subsequent Knoevenagel condensation of 1c (or 3c) with cyanoacetic acid. For the preparation of compounds 2 and 4,5-bromo-2-carbaldehyde was allowed to react with appropriate phenylboronic acid via Suzuki coupling, and with stannyl compound via Stille coupling, respectively, to form intermediates 2b and 4b. Subsequent reactions of the intermediates 2b and 4b with cyanoacetic acid afforded the desired compounds 2 and 4.

The absorption and the emission spectra of compounds 1-4 recorded in THF solution are shown in Table 1.

TABLE 1 optical, redox and DSSC performance parameters of the dyes[a,b]

| Dye | $\lambda_{abs}$, nm ($\epsilon$, $M^{-1} \cdot cm^{-1}$) | $\lambda_{em}$, nm ($\Phi_F$) | $E_{ox}(\Delta E_p)$, mV | $V_{OC}$[d], (V) | $J_{SC}$[e], (mA·cm$^{-2}$) | ff[f] | $\eta$[g] (%) |
|---|---|---|---|---|---|---|---|
| 1 | 469 (33,000) | 608 | 500 (220) | 0.69 | 16.59 | 0.64 | 7.36 |
| 2 | 456 (33,500) | 573 | 570 (140) | 0.68 | 14.16 | 0.66 | 6.30 |
| 3 | 425 (44,900) | 536 | 460 (130) | 0.68 | 14.08 | 0.65 | 6.20 |
| 4 | 459 (35,500) | 592 | 440 (110) | 0.68 | 13.44 | 0.67 | 6.12 |
| N719[c] | | | | 0.73 | 16.77 | 0.63 | 7.69 |

[a]Absorption, emission and electrochemical data were recorded in THF solutions. Scan rate: 100 mV/sec; Electrolyte: (n-C4H9)4NPF6; ΔEp: separation between the anodic and cathodic peaks. Potentials are quoted with reference to the internal ferrocene standard (E½ = +265 mV vs Ag/AgNO3).
[b]Experiments are conducted using TiO2 photoelectrodes with approximately 15 μm thickness and 0.25 cm² working area on the FTO (7 Ω/sq.) substrates.
[c]N719 is a dye prepared from the bivalent anion of the following compound (N3 dye) and tetrabutylammonium ion having 2 equivalent in the related art.

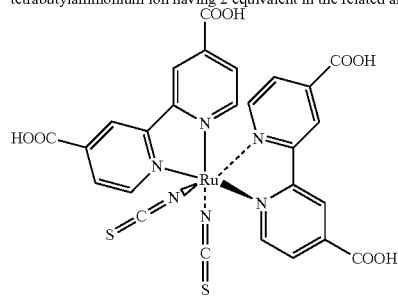

[d]$V_{OC}$: Voltage of open circuit, which is the largest electromotive force provided by the solar cell.
[e]$J_{SC}$: Current of close circuit, which is the largest current when the solar cell is switched on.
[f]ff: Fill factor, which is a ratio of the actually largest powers and theoretically largest powers of a solar cell.
[g]η: Energy conversion efficiency A prominent, band at about 400~600 nm can be attributed to the superposition of π-π* and charge transfer transitions. The charge transfer characteristic in these compounds is also supported by the large Stokes shifts between the absorption and the emission bands (3225~4895 cm$^{-1}$). A negative solvatochromism, i.e., blue shift of the charge transfer band in more polar solvents was noticed in these dyes. For example, the absorption maxima ($\lambda_{max}$) of compound 1 are 485 and 439 nm in toluene and acetonitrile, respectively. This phenomenon can be attributed to the deprotonation of the carboxylic acid, which decreases the strength of the electron acceptor.

A quasi-reversible wave (Eox in Table 1) observed for each compound in the cyclic voltammetry measurements may be arrtibuted to the oxidation of the arylamine. Because of the shorter spacers in compounds 1 and 2, the electron-withdrawing acceptor has greater influence on the arylamine and results in higher oxidation potentials of the arylamines. The excited state potential (E0-0*) of the compounds (−0.74~−0.80 V, which is related to normal hydrogen electrode), deduced from Eox and the zero-zero excitation energy (E0-0) from the absorption band edge, is more negative than the conduction-band-edge energy level of the TiO2 electrode (−0.5 V, which is related to normal hydrogen electrode) and assures that the electron injection process is energetically favourable.

Figure 2:
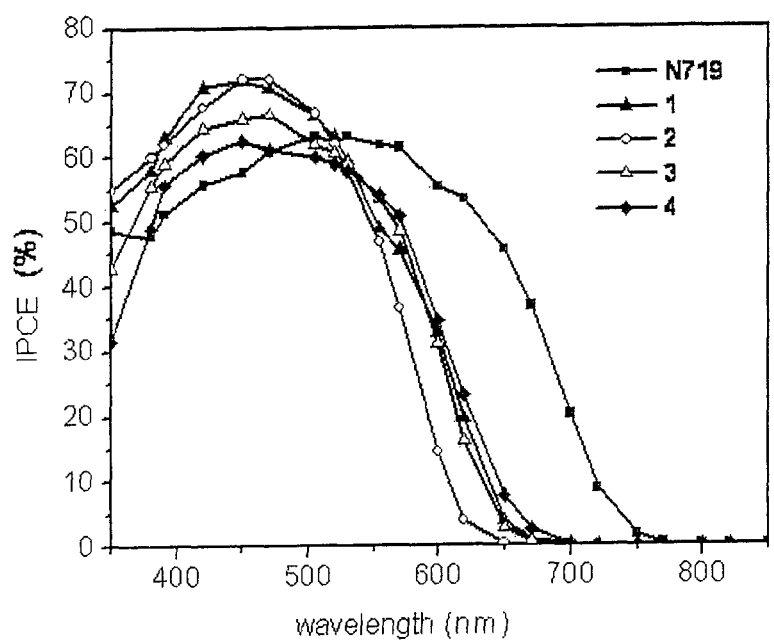
FIG. 2 shows photon-to-current conversion efficiencies (IPCE) of the dyes in examples 1-4 under different wavelengths.

DSSCs are fabricated using these dyes as the sensitizers, with an effective area of 0.25 cm², nanocrystalline anatase TiO2 particles, and the electrolyte composed of 0.05 M I2/0.5M LiI/0.5 M tert-butylpyridine in acetonitrile solution. The DSSC performance statistics under AM 1.5 illumination are listed in Table 1. FIG. 1 shows the photocurrent-voltage (J-V) curves of the solar cells. The incident photon-to-current conversion efficiencies (IPCE) of the dyes on TiO2 are plotted in FIG. 2. The DSSCs exhibit very high conversion efficiencies (6.12%~7.36%) and the best performance of the DSSCs reaches about 96% of a N719-based DSSC (7.69%) fabricated and measured under similar conditions.

The DSSC efficiencies are in the order of compound 1>compound 2>compound 3>compound 4, and several factors may be influential in the DSSC performance: (a) a lower-lying HOMO (estimated 30 from the cyclic voltammetry method) will facilitate reduction of the oxidized dye and suppress back electron transfer from TiO2 to the dye, and consequently lead to larger $V_{OC}$ and $J_{SC}$ (compounds 1 and 2); (b) compounds with better absorption in the longer wavelength region are expected to have better light-harvesting, i.e., compound 1>compound 2; and (c) the higher dye density adsorbed on TiO2 (compound 1, 4.5×10$^{-7}$ mol/cm²; compound 2, 4.1×10$^{-7}$ mol/cm²; compound 3, 3.8×10$^{-7}$ mol/cm²; compound 4, 4.6×10$^{-7}$ mol/cm²) is beneficial to light-harvesting, i.e., compound 1>compound 2>compound 3. The recombination lifetime ($\tau_R$) of the photoinjected electron with the oxidized dye are also measured by transient photovoltage at open circuit. The recombination lifetime ($\tau_R$) of compounds 1, 2, 3, 4 and N719 are respectively 4.9 ms, 5.8 ms, 4.3 ms, 3.1 ms and 10.4 ms. It is found to be in parallel with the trend of the solar cell efficiencies.

A comparison is made on compound 1 and the thiophene congener, 3-5 (5-4-(diphenylamino)styryl)thiophen-2-yl)-2-cyanoacrylic acid (D5). Though D5 has slightly better light-harvesting ($\lambda_{abs}$=476 nm (37600 M$^{-1}$cm$^{-1}$) in MeCN; dye density on TiO2=4.8×10$^{-7}$ mol/cm²) than compound 1 ($\lambda_{abs}$=439 nm (33000 M$^{-1}$ cm$^{-1}$) in MeCN; dye density on TiO2=4.5×10$^{-7}$ mol/cm²), the performance of DSSC based on compound 1 is superior to that based on D5 ($V_{OC}$=0.64 V; $J_{SC}$=14.61 mA/cm²; ff=0.65; η=6.09%) fabricated and measured under similar conditions. Faster recombination lifetime of D5 ($\tau_R$=4.3 ms) may deteriorate the efficiency of the cell. Possible nonbonded intermolecular sulfur-sulfur interaction in D5 may be also deterimental to electron injection of the excited dye into TiO2. Another possibility for the lower efficiency of D5 may be due to the slightly higher tendency of thiophene to trap charge.

In light of the foregoing, the DSSC of the present invention uses the organic dye having furan moiety, and the performance of the organic dye is quite close to that of the ruthenium-based dye. Because ruthenium is not needed in the present invention, the cost of the organic dye and DSSC using the same of the present invention is greatly lower than that of the ruthenium-based dye and ruthenium-based DSSC.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An organic dye used in a dye-sensitized solar cell, having general formula (1):

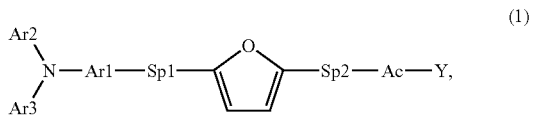

wherein Ar1 represents a substituted or unsubstituted 1,4-phenylene, 2,7-fluorene or 2,7-carbazole, Ar2 and Ar3 each independently represent a substituted or unsubstituted aryl group, Sp1 represent a single bond, vinylene, cyanovinylene or 2,5-thiophene group, Sp2 represent a single bond, Ac represents cyanovinylene, and Y represents an anchoring group, wherein if Ar2 or Ar3 represents a substituted aryl group, a substituted group of the substituted aryl group is selected from the group consisting of alkyl having 1~5 carbon atom(s) and alkoxy having 1~5 carbon atom(s).

2. The organic dye used in a dye-sensitized solar cell as claimed in claim 1, wherein at least one of 2-position and 5-position of 1,4-phenylene is substituted by alkyl or alkoxy having 1-5 carbon atoms.

3. The organic dye used in a dye-sensitized solar cell as claimed in claim 1, wherein 9-position of 2,7-fluorene is substituted by two ethyl groups.

4. The organic dye used in a dye-sensitized solar cell as claimed in claim 1, wherein Ar2 and Ar3 each independently represent a substituted or unsubstituted phenyl, 2-fluorenyl or 1-naphthyl.

5. The organic dye used in a dye-sensitized solar cell as claimed in claim 4, wherein both of Ar2 and Ar3 are phenyl or 2-fluorenyl.

6. The organic dye used in a dye-sensitized solar cell as claimed in claim 1, wherein the anchoring group Y comprises a carboxylic acid group.

7. The organic dye used in a dye-sensitized solar cell as claimed in claim 1, wherein a combination of the acceptor group Ac and the anchoring group Y comprises 2-cyanoacrylic acid group.

8. The organic dye used in a dye-sensitized solar cell as claimed in claim 1, wherein the organic dye has formula (2):

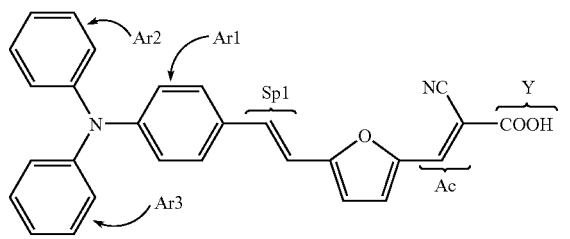

wherein 4-positions of Ar2 and Ar3 are each independently substituted by alkyl having 1~5 carbon atom(s) or alkoxy having 1~5 carbon atom(s).

9. The organic dye used in a dye-sensitized solar cell as claimed in claim 1, wherein the organic dye has formula (3):

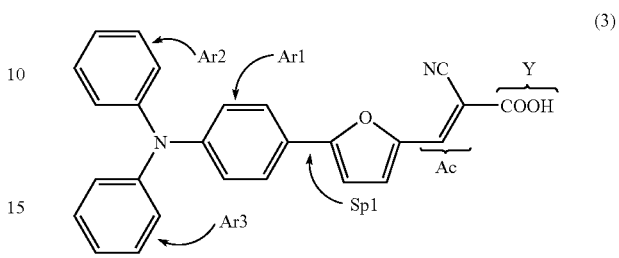

wherein 4-positions of Ar2 and Ar3 are each independently substituted by alkyl having 1~5 carbon atom(s) or alkoxy having 1~5 carbon atom(s).

10. The organic dye used in a dye-sensitized solar cell as claimed in claim 1, wherein the organic dye has formula (4):

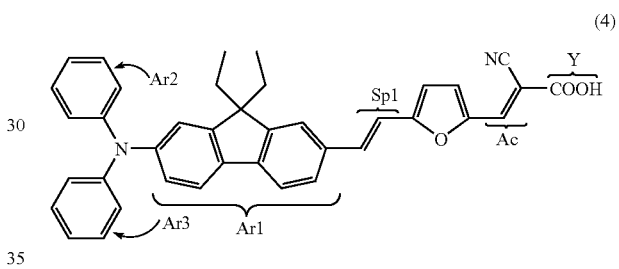

wherein 4-positions of Ar2 and Ar3 are each independently substituted by alkyl having 1~5 carbon atom(s) or alkoxy having 1~5 carbon atom(s).

11. The organic dye used in a dye-sensitized solar cell as claimed in claim 1, wherein the organic dye has formula (5):

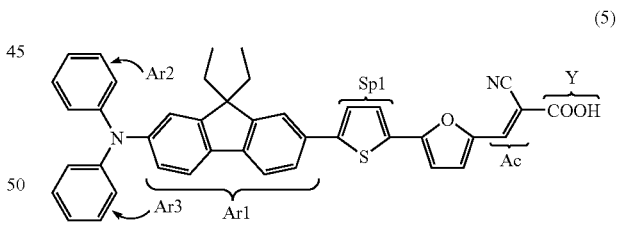

wherein 4-positions of Ar2 and Ar3 are each independently substituted by alkyl having 1~5 carbon atom(s) or alkoxy having 1~5 carbon atom(s).

12. A dye-sensitized solar cell comprising an organic dye of claim 1, an electrolyte and photo-electrodes.

* * * * *